(12) United States Patent
Sonnek et al.

(10) Patent No.: US 9,221,735 B2
(45) Date of Patent: Dec. 29, 2015

(54) PROCESS OF DISTILLING ETHANOL USING AN AIR-COOLED CONDENSER

(76) Inventors: Daniel W. Sonnek, Lake Crystal, MN (US); Gregory W. Loest, Utica, SD (US)

( * ) Notice: Subject to any disclaimer, the term of this patent is extended or adjusted under 35 U.S.C. 154(b) by 507 days.

(21) Appl. No.: 13/219,014

(22) Filed: Aug. 26, 2011

(65) Prior Publication Data

US 2012/0048716 A1    Mar. 1, 2012

Related U.S. Application Data

(60) Provisional application No. 61/377,292, filed on Aug. 26, 2010.

(51) Int. Cl.
C07C 29/80 (2006.01)
B01D 3/00 (2006.01)
F28B 1/06 (2006.01)
B01D 5/00 (2006.01)

(52) U.S. Cl.
CPC .............. C07C 29/80 (2013.01); B01D 3/002 (2013.01); B01D 3/003 (2013.01); B01D 5/006 (2013.01); B01D 5/0054 (2013.01); F28B 1/06 (2013.01)

(58) Field of Classification Search
CPC ........ B01D 3/001; B01D 3/002; B01D 3/003; B01D 3/004; B01D 3/005; B01D 3/42; B01D 5/0057–5/006; B01D 5/0006; B01D 5/0054; C07C 29/74–29/80; C07C 31/08; C07C 7/13; F28B 1/06; F01K 9/00; F28D 1/024
See application file for complete search history.

(56) References Cited

U.S. PATENT DOCUMENTS

| | | | | |
|---|---|---|---|---|
| 3,689,367 A * | 9/1972 | Kassat et al. | ............... | 202/185.3 |
| 4,098,005 A * | 7/1978 | Wiarda | .............................. | 34/73 |
| 4,253,516 A * | 3/1981 | Giardina | ........................ | 165/78 |
| 4,389,797 A * | 6/1983 | Spigarelli et al. | ................. | 34/73 |
| 4,404,062 A * | 9/1983 | Whitehurst | ............... | 202/185.3 |
| 4,489,508 A * | 12/1984 | Carlson et al. | .................... | 34/78 |
| 5,262,013 A * | 11/1993 | Beal et al. | ........................ | 203/18 |
| 5,371,950 A * | 12/1994 | Schumacher | ..................... | 34/78 |
| 5,653,281 A * | 8/1997 | Berg et al. | ..................... | 165/113 |
| 5,824,836 A * | 10/1998 | Becquet | ........................ | 585/800 |
| 2009/0166172 A1* | 7/2009 | Casey | ............................. | 203/19 |
| 2010/0151550 A1* | 6/2010 | Signes Nunez et al. | ....... | 435/165 |
| 2010/0314238 A1* | 12/2010 | Frolov et al. | .................... | 203/10 |

* cited by examiner

*Primary Examiner* — Virginia Manoharan
(74) *Attorney, Agent, or Firm* — Barbara A. Wrigley; Oppenheimer Wolff & Donnelly LLP

(57) ABSTRACT

The present invention is directed towards a process of condensing ethanol during the distillation stage of ethanol production by using an air-cooled condenser. Typically ethanol producing facilities use water-cooled condensers to cool the vaporized ethanol into liquid ethanol. However this water-cooled condenser uses about 50% of the water used in the cooling tower and requires replacement. Due to growing concerns and scrutiny of water usage in the ethanol producing industry air-cooled condensers in the distillation step of ethanol production can significantly conserve water.

3 Claims, 4 Drawing Sheets

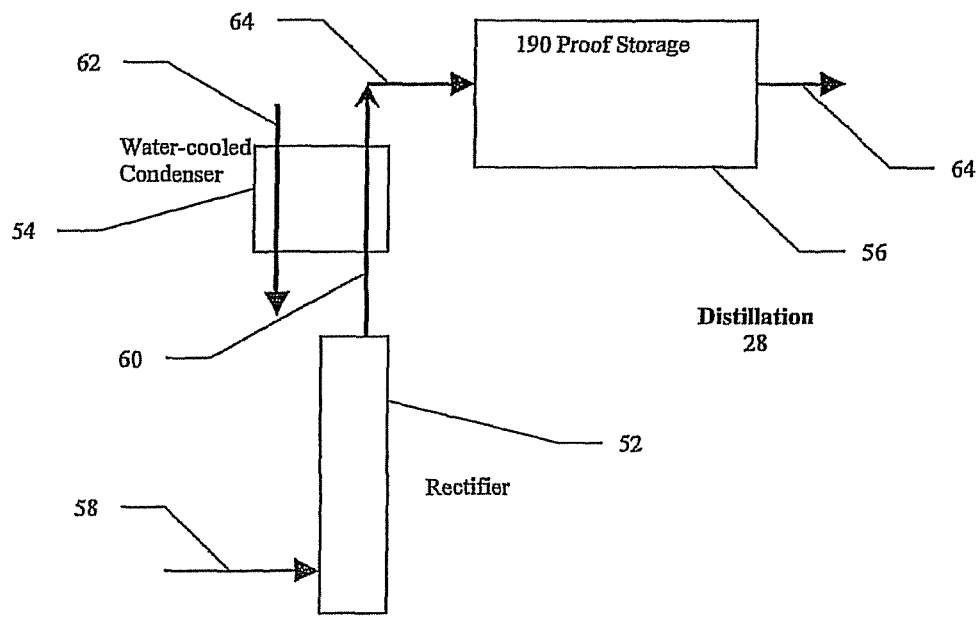
FIG. 2 - *Prior Art*
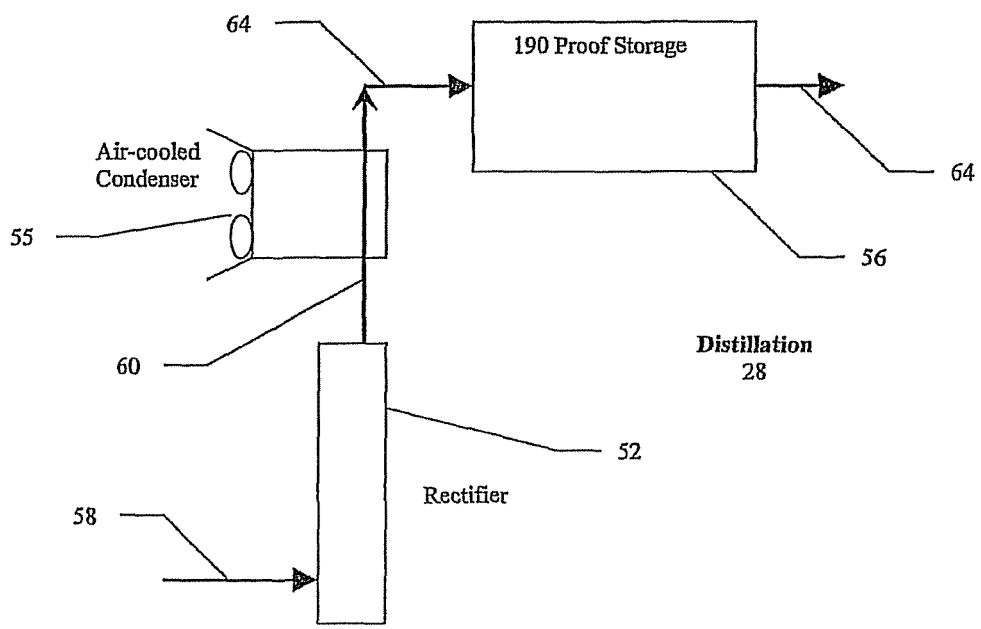
FIG. 3

FIG. 4 – *Prior Art*

PROCESS OF DISTILLING ETHANOL USING AN AIR-COOLED CONDENSER

CROSS REFERENCE TO RELATED APPLICATIONS

This application claims the benefit of U.S. Provisional Application Ser. No. 61/377,292, filed Aug. 26, 2010, the entirety of which is hereby incorporated by reference.

FIELD OF THE INVENTION

The present invention is generally directed to ethanol processing. More particularly, the present invention is directed to an improved process for heat removal during ethanol production.

BACKGROUND OF THE INVENTION

Over the past thirty years, significant attention has been given to the production of ethyl alcohol, or "ethanol," for use as an alternative fuel. Ethanol not only burns cleaner than fossil fuels but also can be produced using grains such as corn, which is a renewable resource. Further, the production of ethanol results in new sales outlets for corn, provides additional jobs, and reduces the nation's dependency on foreign oil.

Ethanol is typically produced from corn through either a wet or dry milling process. In the wet milling process, the corn kernel is separated into various components including germ, starch, protein, and fiber, resulting in several co-products. For example, separated germ may be further processed for oil recovery; starch may be saccharified and fermented for ethanol production; and protein and fiber may be used as feed material. In a dry mill process, whole corn is ground, treated with enzymes, and cooked. The resulting "mash" is treated with enzymes to further break down the starchy endosperm tissue into glucose. The converted mash is fermented and distilled, producing ethanol, carbon dioxide, and distiller's dried grains ("DDG"), which are the undissolved solid components (i.e. stillage) remaining in the fermentation tank after the broth is removed. Thus, DDGs are typically comprised of yeast and unfermented components of the corn.

The dry grind process converts corn into two products, including ethanol and distiller's grains with solubles. If sold as wet animal feed, the co-product is known as distiller's wet grains with solubles ("DWGS"). Conversely, if dried for animal feed, the co-product is known as distiller's dried grains with solubles ("DDGS"). In the standard dry grind ethanol process, one bushel of corn yields approximately 8.2 kilograms (i.e. approximately 18 pounds) of DDGS in addition to the approximately 10.2 liters (i.e. approximately 2.7 gallons) of ethanol. These co-products provide a critical secondary revenue stream that offsets a portion of the overall ethanol production cost.

Within a typical ethanol production facility, current process technology requires heat be removed from the process at various rates and locations. The standard method for heat removal is with the use of cooling water. This cooling water typically forms part of a closed loop system that picks-up heat via heat exchangers and condensers and is then returned to a cooling tower where the heat is removed via evaporative cooling. The cooling water is then recirculated back to the process.

This evaporative cooling is a major loss of water in the ethanol production facility. Because the water is evaporated, the amount of water in the cooling system is reduced. Thus, in order to keep the proper amount of water in the system, additional make-up water must be introduced. Furthermore, by evaporating water, minerals in the water will concentrate. If this cycling is uncontrolled the minerals will reach levels that will cause harmful deposits within the cooling system. Therefore, a blow down system is typically employed to discard the water with high mineral concentration and replace it with even more clean make-up water. Because there is a great deal of scrutiny in the ethanol industry regarding water use, alternative means of cooling are desirable.

As stated above, heat is extracted from the ethanol production process in numerous areas such as fermenters, vent condensers, propagator coolers, etc. One other exemplary location where water cooling is used is in the distillation area. Typical distillation includes a rectifier column to obtain the highly concentrated ethanol vapors and a condenser that cools the vapors to obtain 95% pure ethanol (i.e. 190 proof ethanol). In many facilities the 190 proof ethanol is condensed directly off the top of the rectifier column typically by a water-cooled condenser. The water-cooled condenser at this point uses approximately 50% of the cooling tower's water and approximately 25% of the entire plant's water. Other facilities do not have a phase change in distillation directly, but instead run the evaporation into a condenser, which is also a significant location of water usage for the facility.

A unique aspect of the distillation stage compared to other stages in the ethanol production process is that the water-cooled condensers can run at significantly higher temperatures than the water-cooled condensers used for other areas of the plant. This is because ethanol vapors condense at high temperatures, more specifically at temperatures 78° C. or less. Other condensers in the ethanol production process require temperatures cooler than the ambient air. Furthermore the heat captured by the water cooling in the distillation stage is not very significant as to make any considerable use of it in the rest of the facility. Therefore, because of the high amount of water usage, the high condensation temperature, and the minimal recyclability of heat, the distillation stage is prime location to replace the water-cooled condensers with an alternative condenser such as an air-cooled condenser.

Although air-cooled condensers themselves are not novel and used in place of water-cooled condensers in many industries including the ethanol production industry as exemplified in U.S. Pat. Application Publication No. 2009/0166172, they could be implemented in the distillation stage to reduce the use of water and correct for some of the issues that arise from water usage. Since the temperature required during the distillation step is 78° C. or less, it is a prime location for an air-cooled condenser because the distillation condensation requires temperatures that rarely exceed ambient temperature anywhere on Earth. Other condensers in the plant may require temperatures that are less than the ambient air. Therefore an air-cooled condenser may not be appropriate there.

Therefore, what is needed is an ethanol distillation process that employs an air-cooled condenser for extracting ethanol from an ethanol vapor stream in an effective manner as to reduce the usage of water in the ethanol production facility.

BRIEF SUMMARY OF THE INVENTION

The present invention addresses the foregoing problems by providing an ethanol distillation process that includes pumping fermented beer into a rectifier and heating the beer to a temperature where ethanol vaporizes. Thereafter, the vaporized ethanol is directed into an air-cooled condenser that condenses the ethanol vapor into liquid form. From there it is either stored for later purification from 95% ethanol to 100% ethanol or sent directly to a purification step.

BRIEF DESCRIPTION OF THE DRAWINGS

FIG. 2 is a circuit diagram of a typical distillation step for manufacturing ethanol where a water-cooled condenser cools the ethanol vapor from the rectifier.

FIG. 3 is a circuit diagram of the distillation step where the water-cooled condenser is replaced with an air-cooled condenser.

DETAILED DESCRIPTION OF THE INVENTION

The present invention is directed to an improved process of distilling ethanol as to reduce or eliminate water usage in the distillation step of ethanol production. The process replaces a traditional water-cooled condenser, which changes vaporized ethanol to liquid ethanol, with an air-cooled condenser. The 95% liquid ethanol is then pumped to a purification stage to obtain 100% ethanol.

As stated above, this is one exemplary use of the method of the present invention for condensing a vaporized substance into liquid form. The process of the present invention may be used for condensing vaporized substances during any agricultural or petroleum product processing without departing from the intended scope of the present invention.

Figure 1:
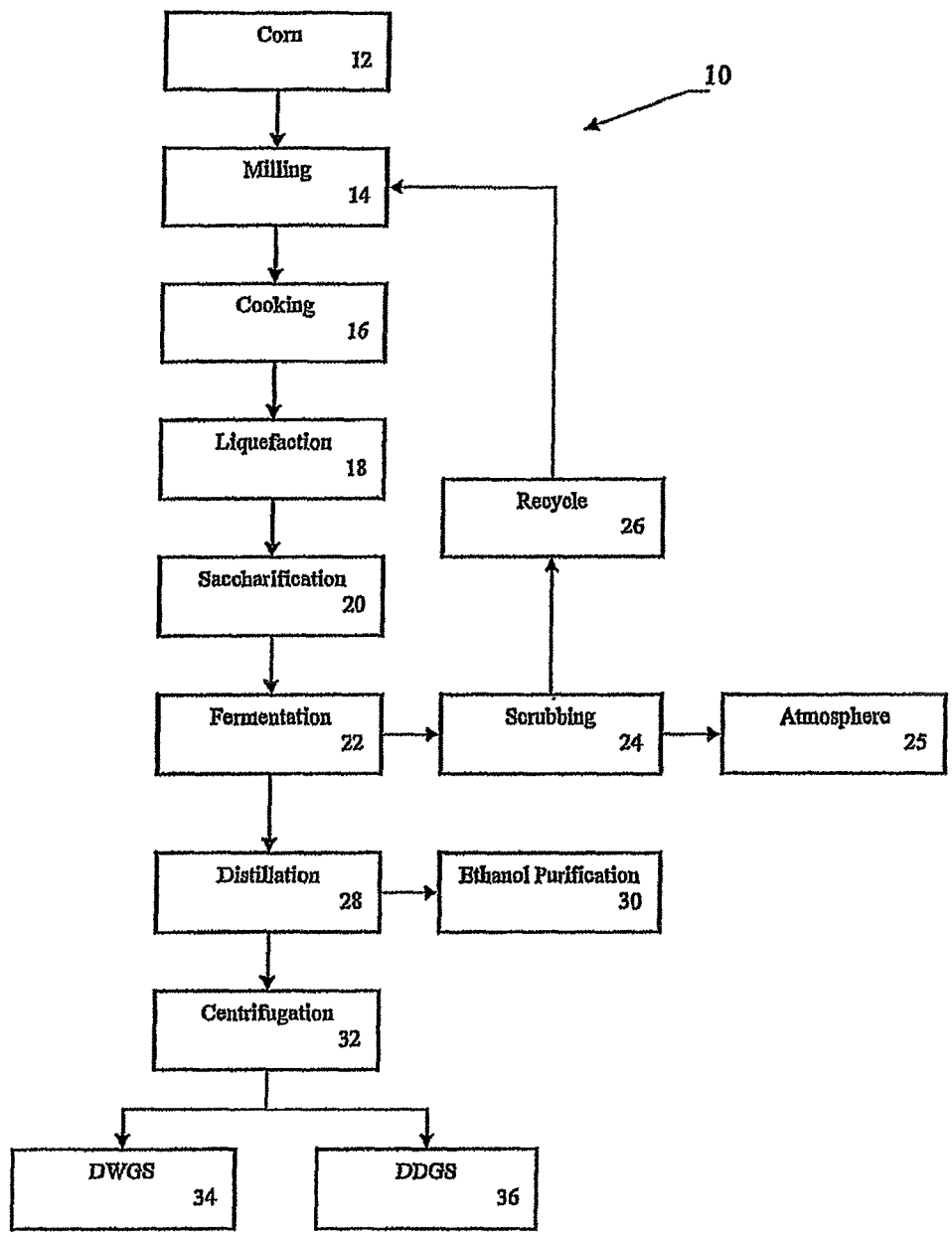
FIG. 1 is a flow diagram illustrating a typical dry grind process for manufacturing ethanol.

FIG. 1 is a flow diagram illustrating a typical dry grind ethanol process 10. The process 10 begins at step 12 where the type of grain that will be used for ethanol production is selected. Because corn is the most common grain that is used for the production of ethanol, the dry grind process 10 will be described with reference to corn for purposes of example and not limitation. Although virtually any type and quality of corn may be used, one common type of corn is known as "No. 2 Yellow Dent Corn." The "No. 2" refers to a quality of corn having certain characteristics as defined by the National Grain Inspection Association as generally known in the art. "Yellow Dent" refers to a specific type of corn as also generally known in the art. The industry average for ethanol yield in a dry grind plant is approximately 10.2 liters (i.e. approximately 2.7 gallons) of ethanol produced per 25.4 kilograms (i.e. one bushel) of No. 2 Yellow Dent Corn.

The process continues with a milling step 14 wherein dried whole corn kernels are passed through hammer mills in order to grind the kernels into meal or a fine powder. The ground meal is mixed with a suitable liquid, such as water, to create a slurry. Additionally, a commercial enzyme known as alpha-amylase may be added to the slurry. This slurry is then heated in step 16 to temperatures above 100° C. and allowed to cook in a pressurized "jet cooking" process. Jet cooking refers to a cooking process performed at elevated temperatures and pressures. The jet cooking process helps to break apart the starch granules present in the endosperm of the kernel, and the added enzymes function to break down the starch polymer into small fragments. Thus, the starch becomes gelatinized.

The cooked corn mash is then allowed to cool and is held at a temperature between about 80° C. and about 95° C. in a liquefaction step 18. During the liquefaction step 18, additional alpha-amylase may also be added. As appreciated by those skilled in the art, holding the mash at the lower temperature allows the alpha-amylase to hydrolyze the gelatinized starch into maltodextrins and oligosaccharides (i.e. chains of glucose sugar molecules) to produce a liquefied mash or slurry.

The liquefaction step 18 is followed by a saccharification step 20 and a fermentation step 22. As will be appreciated by those skilled in the art, these two steps may be combined and occur simultaneously in many commercial dry grind ethanol systems. When combined, these steps are referred to in the industry as "simultaneous saccharification and fermentation." In the saccharification step 20, the liquefied mash is first cooled to about 30-50° C. Then, a second enzyme known as glucoamylase is added. The addition of glucoamylase to the liquefied mash completes the breakdown of the starch into simple sugar (i.e. glucose). The saccharification step 20 may occur while the fermentation vessel is being filled with the mash in preparation for the fermentation step.

In the fermentation step 22, yeast is added to the corn mash to begin the process of metabolizing the simple sugars into ethanol. As will be appreciated by those skilled in the art, a common strain of yeast known as Saccharomyces cerevisae is typically chosen due to its quick and efficient production of ethanol. The mixture of yeast and corn mash is fermented for approximately two days to allow the simple sugars to be converted into (1) ethanol and (2) carbon dioxide. The other components of the corn mash, including protein and oil, are substantially unchanged by the fermentation process. After fermentation, the fermentation mash ("beer") will contain about 8-12% ethanol by weight, plus soluble and insoluble solids from the remaining grain components.

The carbon dioxide produced in the fermentation vessel may then be vented to and passed through a scrubber in step 24 to remove ethanol vapors and VOCs prior to releasing the stream to the atmosphere in step 25. The scrubber typically utilizes fresh water along with a variety of additives to increase the solubility of the ethanol and VOCs. The precipitate of the scrubber is water with a low concentration of ethanol. This scrubber water may be recycled back into the process in step 26 by directing the water into the slurry tank where the ground corn meal is mixed with liquid to create the slurry. Alternatively, the scrubber water may be recycled back into the process at another suitable location, such as in a distillation tank during a subsequent distillation step.

The beer contained within the fermentation vessel is then sent to a distillation vessel in step 28 for distillation and dehydration. Optionally, the beer may be stored in a "beer well" prior to being sent to the distillation vessel. The beer well may be used to store the fermented beer and supply a controlled stream of beer to the distillation vessel at specified times. As appreciated by those skilled in the art, distillation is the process of separating mixtures based on differences in there volatilities in a boiling liquid mixture. Thus, distillation is a physical separation process and not a chemical reaction. At sea level, water vaporizes at 100° C. while alcohol vaporizes at about 78° C. This difference in vaporization temperature allows for the separation of water from ethanol upon heating the mixture in a distillation vessel.

More particularly, in the distillation step 28 fermented beer 58 is pumped into the rectifier 52 where it is boiled to vaporize the ethanol. The ethanol vapor 60 is condensed in the rectifier or outside of it, and liquid ethanol exits the condenser at about 95% purity (i.e. 190 proof) where it is directed into an ethanol purification unit at step 30. The distillation process may also produce a vent stream comprised of carbon dioxide and ethanol, which may be directed through the scrubber along with the vapors produced in the fermentation step 22. Thus, the ethanol that is scrubbed from both the fermentation and distillation vent streams may be recycled back into the process in any suitable manner as previously discussed.

In order to create an ethanol/gasoline blend, it is necessary to remove the roughly 5% of water that remains in the liquid ethanol. This may be accomplished by passing the 95% pure ethanol through a molecular sieve dehydration column to remove the residual water and create a final product that is almost 100% ethanol (i.e. roughly 200 proof). The resulting anhydrous ethanol is then ready to be used for motor fuel purposes. However, the anhydrous ethanol is commonly blended with another petroleum product, such as gasoline, prior to being used as a motor fuel.

The combination solid and liquid product that remains after the distillation step 28 is known as "whole stillage." As appreciated by those skilled in the art, whole stillage may include, among other components, non-fermented starch and the protein, oil, and fiber components of the corn. Whole stillage is a valuable co-product of ethanol processing because it may be used as a feed ingredient for animals, which helps ethanol producers to offset the cost of ethanol production. Although the whole stillage may be used as a feed ingredient without further modification, it typically undergoes further processing prior to being fed to animals. In one exemplary method of processing the whole stillage, the stillage is sent through a centrifugation step 32 in order to separate the insoluble solids or "wet cake" from the liquid or "thin stillage." After centrifugation, the thin stillage and wet cake may be used to create several types of feed, including DWGS at step 34 and DDGS at step 36.

In order to produce the DWGS, the thin stillage may be sent to an evaporator to boil away moisture, leaving a thick syrup containing the dissolved solids from the fermentation step. This concentrated syrup may be mixed with the centrifuged wet cake, and the mixture may be sold as DWGS to animal feedlots. Alternatively, in order to produce the DDGS, the wet cake and concentrated syrup mixture may simply be dried with any suitable drying means and sold to animal feedlots.

FIG. 2 is a circuit diagram illustrating an embodiment of a water-cooled distillation step 28 as described in detail above with reference to FIG. 1. Particularly, fermented beer 58 is pumped into the rectifier 52 where it is heated and ethanol vapor 60 is produced. The ethanol vapor 60 passes through a water-cooled condenser 54 where the ethanol vapor 60 is cooled to form liquid ethanol 64 of 95% purity. This liquid ethanol 64 is stored in the 190 proof storage vessel 56 where it will then be sent to the ethanol purification step 30. The water 62 entering the water-cooled condenser 54 comes from the facility's cooling tower directly or from another part of the ethanol producing facility and eventually returns to the cooling tower. Typically when the heated water 62 is returned to the cooling tower the heat is removed through evaporative cooling before being recirculated back to the process. This evaporative cooling is a major loss of water in the ethanol producing facility since the water is evaporated. Additionally, evaporation will concentrate the minerals in the cooling water and if this cycling is uncontrolled the minerals will reach levels that will cause harmful deposits within the cooling system. Therefore, a blow down system is employed to discard the water with high mineral concentration and replace it with even more clean make up water.

Water usage is a source of scrutiny in the ethanol industry. There are a number of environmental factors such as effects on aquatic life and its availability in water poor areas. Furthermore there are a number of economic drawbacks to water usage. The need for high quantities of water can limit the location of a new ethanol facility to areas close to significant sources of water, which may be more expensive. Also the time it takes and delays in obtaining water rights adds to the cost of building an ethanol facility and cost of water through taxes may be high in certain regions. Climate similarly has a negative impact on water-cooling. If the plant were to shut down in the winter time due to some emergency situation, there is a possible threat of the cooling water freezing causing pipes carrying the water to burst and delaying production further until ice filled pipes can be unthawed. Therefore it is beneficial to find alternative ways to cool different processes of ethanol plants besides using water. The distillation step 28 as previously described requires a significant amount of water. Water usage during the distillation step 28 by the use of water-cooled condensers 54 accounts for 50% of the load on the cooling tower. Eliminating the need for any cooling water in this application will potentially reduce the water used by the cooling tower by 50% and the entire facility by 25% or more. Additionally, the amount of cooling tower blowdown (or discharge) to the environment is reduced by this proportion.

As will be described in further detail to follow, the present invention is an improvement to the water-cooling process of the distillation step 28 by using air-cooled condensers 55 to turn ethanol vapor 60 into liquid form. Ideally it would be beneficial to use air-cooling throughout the ethanol facility to eliminate the use of water entirely from the cooling process. However, as known to one skilled in the art the entire plant cannot be air-cooled because many areas must be cooler than the ambient air temperature. This would include fermenters, vent condensers, propagator cooler, etc. However, the distillation step 28 has condensers that run at significantly higher temperatures than ambient air. More specifically ethanol vapors 60 condense at temperatures of 78° C. Therefore an air-cooled condenser 55 would be effective at the distillation step 28 anywhere on Earth.

FIG. 3 is a circuit diagram illustrating an exemplary embodiment of the current invention where the water-cooled condenser 54 of FIG. 2 is replaced by an air-cooled condenser 55. Particularly, fermented beer 58 is pumped into the rectifier 52 where it is heated and ethanol vapor 60 is produced. The ethanol vapor 60 passes through an air-cooled condenser 55 where the ethanol vapor 60 is cooled to form liquid ethanol 64 of approximately 95% purity. This liquid ethanol is stored in the 190 proof storage vessel 56 where it will then be sent to the ethanol purification step 30 to obtain 100% pure ethanol.

Figure 4:
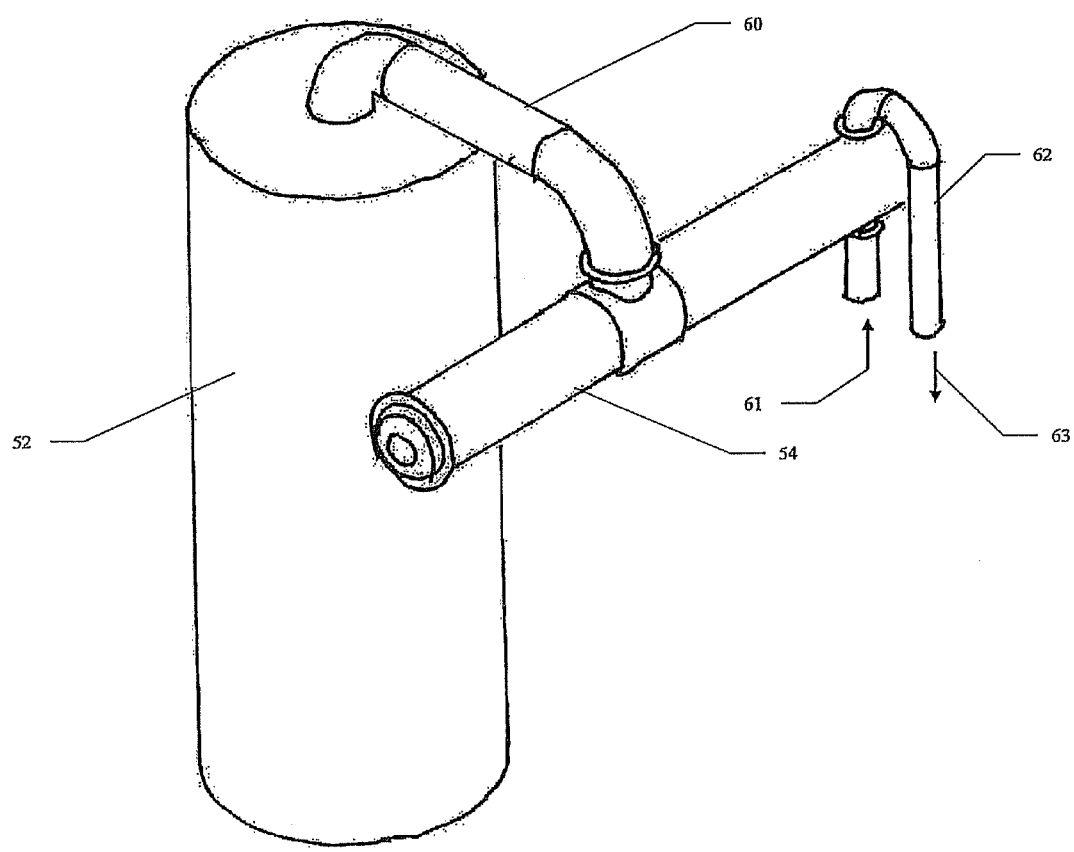
FIG. 4 is an exemplary embodiment of the ethanol industry's current ethanol distillation where the ethanol vapor is condensed by a water-cooled condenser.

FIG. 4 is an exemplary embodiment of a current distillation step 28 utilizing a water-cooled condenser 54. A rectifier 52 is in fluid communication with the water-cooled condenser 54 as to allow the ethanol vapor 60 to flow to the water-cooled condenser 54 from the rectifier 52. The ethanol vapor outlet from the rectifier is located on the vertical end of the rectifier 52 since ethanol vapor rises. The water-cooled condenser 54 has at least one ethanol vapor inlet flow supply line and also a water inlet flow supply line 61. The water-cooled condenser also has a liquid ethanol outlet flow line and a water outlet flow line 63. Water is pumped through the water-cooled condenser 54 while the ethanol vapor 60 is present. Cooling the ethanol vapor condenses it to liquid ethanol 64 of 95% purity. Where then the heated water 62 is passed out of the water-cooled condenser 54 through the water outlet flow line 63 and returns to the cooling tower for cooling. The liquid ethanol 64 of 95% purity as it collects exits the liquid ethanol outlet flow line to the 190 proof storage 56 or directly to the ethanol purification step 30 to obtain 100% ethanol.

Figure 5:
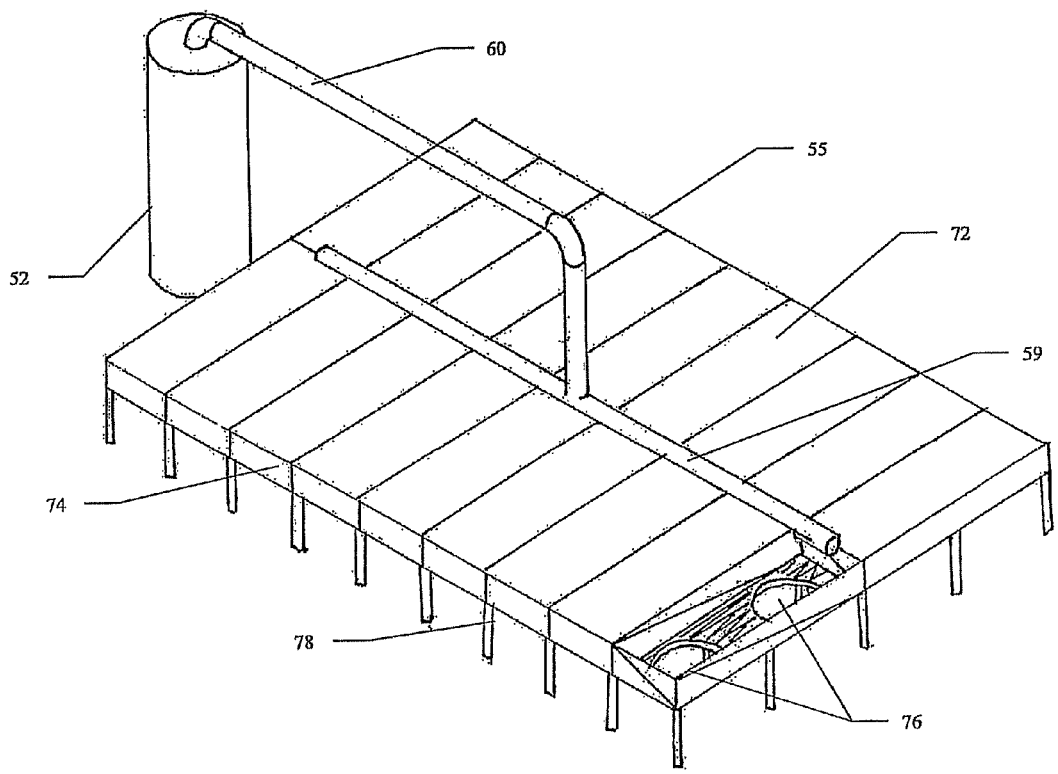
FIG. 5 is an exemplary embodiment of the current invention using an air-cooled condenser to condense the ethanol vapor from the rectifier.

FIG. 5 is an exemplary embodiment of the present invention, a process for distilling ethanol using an air-cooled condenser 55. As explained previously in FIG. 3 fermented beer 58 is pumped into the rectifier 52 where it is heated and ethanol vapor 60 is produced. The ethanol vapor 60 passes through an air-cooled condenser 55 where the ethanol vapor 60 is cooled to form liquid ethanol 64 of 95% purity.

More specifically an exemplary embodiment of the distillation step is as follows. Fermented beer 58 enters the rectifier 52 through a beer inlet flow supply line at the bottom of the rectifier 52 where it is heated to where the ethanol vaporizes and is directed towards the top of the rectifier 52. The rectifier 52 contains an ethanol vapor outlet flow line 59 which is in fluid communication with the air-cooled condenser 55 by a piping system. The air-cooled condenser 55 comprises of a plurality of individual condenser modules 72. Each individual module 72 comprises of a structural support portion 78 to give support for each condenser module 72 and the air-cooled condenser 55 as a whole. The support portion 78 raises the module off the surface it resides on as to allow for adequate air flow beneath each condenser module 72. Each condenser module 72 has an inlet flow supply line that is in fluid communication with the cooling coils 74 and each inlet flow supply line is in fluid communication with ethanol vapor outlet flow supply line 59 to supply the condenser modules 72 with ethanol vapor 60. A liquid ethanol outlet flow line is in fluid communication with the cooling coils 74 to gather and store the 95% pure liquid ethanol or pump it directly to the ethanol purification step 30. In the present embodiment blowers 76 or fans are placed below the cooling coils 74 and directed upward to pass air over the cooling coils 74 to remove heat from the coils. FIG. 5 shows the removal of the cooling coils 74 in one of the condenser modules 72 to show the blowers 76 in relation to the coils. As the ethanol vapor 60 enters each individual condenser module 72 it passes through the cooling coils 74, which have a high surface area. This high surface area allows heat to transfer from the heated ethanol vapors 60 to the cooling coils 74. The heat is then transferred from the cooling coils 74 to the surrounding air. The blowers 76 are used to remove the heated air near the cooling cools 74 with cooler ambient air.

Although the present invention has been described with reference to select embodiments, workers skilled in the art will recognize that changes may be made in form and detail without departing from the spirit and scope of the invention.

What is claimed is:

1. A process of distilling ethanol in an ethanol production facility comprising:
    pumping ethanol into a rectifier through an inlet flow supply line positioned at the bottom of said rectifier, said rectifier including an ethanol vapor outlet flow line;
    heating said ethanol to produce ethanol vapor, wherein said ethanol vapor is directed to said ethanol vapor outlet flow line;
    providing an air cooled condenser, said air cooled condenser including a plurality of individual condenser modules, each of which has cooling coils and a condenser inlet flow supply line, said cooling coils in fluid communication with the condenser inlet flow supply line;
    positioning at least one air blower below said cooling coils for directing air over the cooling coils to remove heat therefrom;
    receiving a stream of ethanol vapor by said condenser inlet flow supply line from a said ethanol vapor outlet flow line;
    condensing the stream of ethanol vapor to liquid ethanol during a distillation step by passing said ethanol vapor through said air-cooled condenser cooling coils thereby eliminating the need to cool said ethanol vapor with a water cooled condenser thus
    reducing the use of water in the ethanol production facility by more than 25%; and
    storing the liquid ethanol in a storage medium, wherein the air used to cool the air-cooled condenser is at a temperature of 78° C. or less.

2. A process as claimed in claim 1, further comprising the step of: pumping the stored liquid ethanol to a dehydration system.

3. A process as claimed in claim 1, further comprising reducing the load on a water-cooling tower used in the ethanol production facility by 50%.

* * * * *